United States Patent [19]
Hani

[11] Patent Number: 5,782,776
[45] Date of Patent: Jul. 21, 1998

[54] GUIDEWIRE ATTACHMENT ASSEMBLY

[75] Inventor: Robert Hani, Unterlunkhofen, Switzerland

[73] Assignee: Schneider A.G., Bulach, Switzerland

[21] Appl. No.: 747,409

[22] Filed: Nov. 12, 1996

Related U.S. Application Data

[62] Division of Ser. No. 442,714, May 11, 1995, Pat. No. 5,605,163.

[30] Foreign Application Priority Data

May 11, 1994 [EP] European Pat. Off. ............ 94107357

[51] Int. Cl.⁶ ............................................. A61B 5/00
[52] U.S. Cl. ................... 600/585; 600/434; 604/280; 604/281
[58] Field of Search .......................... 600/585; 604/95, 604/96, 200, 281, 282

[56] References Cited

U.S. PATENT DOCUMENTS

| | | | |
|---|---|---|---|
| Re. 34,466 | 12/1993 | Taylor et al. | 128/657 |
| 4,827,941 | 5/1989 | Taylor et al. | 128/657 |
| 4,846,193 | 7/1989 | Tremulis et al. | 128/772 |
| 4,917,103 | 4/1990 | Gambale et al. | 128/772 |
| 5,113,872 | 5/1992 | Jahrmarkt et al. | 128/772 |
| 5,139,032 | 8/1992 | Jahrmarkt et al. | 128/772 |
| 5,188,621 | 2/1993 | Samson | 604/283 |
| 5,197,486 | 3/1993 | Frassica | 128/772 |
| 5,234,002 | 8/1993 | Chan | 128/772 |
| 5,247,942 | 9/1993 | Prather et al. | 128/772 |
| 5,404,886 | 4/1995 | Vance | 128/772 |
| 5,605,163 | 2/1997 | Hani | 128/772 |

FOREIGN PATENT DOCUMENTS

| | | |
|---|---|---|
| 0321796 | 6/1989 | European Pat. Off. . |
| 92/18051 | 10/1992 | WIPO . |
| 93/03664 | 3/1993 | WIPO . |

*Primary Examiner*—Max Hindenburg
*Assistant Examiner*—Pamela J. Wingood
*Attorney, Agent, or Firm*—Peter C. Richardson; Lawrence C. Akers; Philip C. Strassburger

[57] ABSTRACT

The guidewire attachment assembly comprises a tubing affixed to the proximal end of a guidewire. Inside the tubing is a shoulder and a ramp for directing and positioning a bolt arranged at the end of a resilient shaft affixed to the distal end of the extension wire. The assembly provides a positive locking action for the guidewire and extension wire and direct unlocking thereof.

26 Claims, 4 Drawing Sheets

GUIDEWIRE ATTACHMENT ASSEMBLY

This is a division, of application Ser. No. 08/442,714, filed on May 11, 1995 now U.S. Pat. No. 5,605,163.

BACKGROUND OF THE INVENTION

This invention relates to vascular procedures and more particularly to a docking assembly for the extension of a guidewire with an extension wire comprising socket means and plug means for axial engagement into said socket means.

It is common practice to use a guidewire for the placement of a catheter in vascular procedures such as angioplasty. A guidewire typically is slightly longer than the catheter with which it is used, whereby a relatively short portion of the guidewire protrudes proximally from the catheter when the catheter is in place. If it becomes necessary to exchange the catheter, for instance to increase the balloon size in an angioplasty procedure, the guidewire must be removed and replaced by an exchange wire which is about twice the length of the catheter in order to allow withdrawal of the catheter and insertion of a new catheter over the exchange wire. However, this technology seriously complicates and slows down the vascular procedure, and there have been several attempts to attach an extension wire to the initial guidewire in order to eliminate the need of a separate exchange wire.

European Patent No. 0321796 A2 describes an extendable guidewire system comprising a main guidewire section and a guidewire extension section and a connection therebetween including a tubular member fixed to the end of one of the guidewire sections and a male member arranged on the end of the other guidewire section which has a maximum radial dimension which is greater than the inner diameter of the tubular member, whereby the male member may be inserted into the tubular member to releasably secure the two guidewire sections together. According to a first embodiment, the male member is shaped into an undulating or sinusoidal shape. According to a second embodiment, the male member is provided with a smaller diameter portion having radial protrusions.

Hence, deformation of the undulating shape of the male member or relative deformation of the male member with radial protrusions provide for a friction fit of the male member into the tubular member and the two guidewire sections may be connected or disconnected as desired. The need for radial deformation to generate the friction fit requires a distinct difference in diameter between the inner diameter of the tubular member and that of the male member. Therefore, the male member has to be extremely thin and it may be easily bent inadvertently, thereby ruining the guidewire section to which it belongs. Furthermore, as the insertion of the male member into the tubular member is made against friction forces, these forces may cause buckling, and even total kinking in the case of a male member with sinusoidal shape, also ruining the corresponding guidewire section.

U.S. Pat. No. 4,917,103 shows a guidewire system in which a steel tubular connector is attached to the proximal end of a guidewire and a reduced diameter steel tip is attached to the distal end of an extension wire. The contrary is also possible, with the tubular connector on the extension wire and the reduced diameter tip on the guidewire. For connecting the extension wire to the guidewire, the reduced diameter tip is inserted into the tubular connector and the assembly of both the tip and connector is crimped by means of appropriate pliers used as a crimping tool. Mechanical attachment of both parts is thus obtained by displacing a segment of both the tubular connector and tip inserted therein laterally of their common axis in what may be considered as a generally U-shaped configuration. The extent of lateral displacement is of course selected so that it will not interfere too much with the smooth advancement of a catheter over the point of assembly. To release or disconnect the assembly of guidewire and extension wire, it is necessary to cut the guidewire distally of the crimp or to break the connection at the location of the crimped tubular connector and tip assembly. The system is thus a permanent connection, and when released by cutting the guidewire or breaking the connector and tip assembly, both the guidewire and extension wire are ruined, so that the system is definitely not re-usable. In addition, the cutting-out of the guidewire or the breaking of the connector and tip assembly may prove difficult or even impossible without some special cutting tool. And this adds to the fact that the need to use a crimping tool for the mechanical attachment of the tubular connector and tip renders the system dependent from the proper use of the crimping tool.

U.S. Pat. No. 5,188,621 disclosed an extendable guidewire assembly in which the guidewire has a tapered proximal end, the extension wire has a tapered distal end, and a polymeric tubular sleeve is affixed concentrically about one of either the proximal end of the guidewire or the distal end of the extension wire. The sleeve is so made as to have its lumen expanding radially when the sleeve is under axial compression and to contract radially when the sleeve is under axial tension; furthermore, the lumen of the sleeve has a diameter which is smaller than the untapered diameter of the wire to which the sleeve is not fixedly attached. To connect the assembly, the tapered end of the wire to which the sleeve is not fixedly attached is inserted into the sleeve until a tight friction fit between the sleeve and the tapered end is achieved. Because of the so-called "Chinese finger tube" fit, the connection between the sleeve and tapered end inserted therein will be verified upon applying axial tension to both wires; disconnection will be achieved only by placing a gripping force on the end face of the sleeve in which is inserted the tapered end of the wire not fixedly attached to the sleeve, and pulling said tapered end from the lumen of the sleeve. This assembly is thus providing a self acting connection which needs however manipulations and skill to be disconnected.

U.S. Pat. No. 5,113,872 describes a guidewire extension system comprising an extension guidewire adapted to be releasably connected to a proximal end of an initial guidewire. The distal end of the extension guidewire is mounted in a tube in which is located an open pitch flat wire coiled spring one end of which is placed over the distal end of the extension guidewire and welded thereto; the other end of the coiled spring extends freely in the tube and a detent arranged at the end of the tube prevents the free end of the spring from being moved out of the tube. To achieve connection of the extension guidewire to the initial guidewire, the ground down proximal end of the initial guidewire is inserted into the tube and urged therein until it engages the coiled flat wire spring and bottoms against the distal end of the extension guidewire. As the proximal end of the initial guidewire is inserted into the coils of the flat wire coiled spring, the coils are forced to slightly uncoil so that they can receive the outer diameter of the proximal end of the initial guidewire. Then, any axial force pulling the proximal end of the initial guidewire away from the coiled spring causes the coils around said proximal end to move towards a smaller diameter and that tendency establishes a connection between the coils and proximal end. Any pull on the extension guidewire causes axial extension of the coiled spring, which results in a reduction of the diameter of the coils and greatly increases the locking forces of the coiled spring against the proximal end of the initial guidewire. To disconnect the assembly it is necessary to rotate the extension guidewire in order to loosen the grip of the coiled spring against the proximal end of the initial guidewire and at the same time to pull the initial guidewire out of engagement with the coils of the flat wire coiled spring. This assembly also provides a self acting connection which is however dependent on manipulations and skills to be disconnected.

U.S. Pat. No. 5,247,942 shows a guidewire arrangement with swivel capacity, comprising a main part, an extension part, and a connector. The connector joins the main part to the extension part such that the main part and extension part may be rotated relative to each other. In one embodiment devised as an attachable extension, the arrangement provides for a socket attached to one of the parts and a plug attached to the other part. The socket comprises a resilient bolting snap which protrudes inwardly of the socket. The plug is terminated by a cylindrical part forming a circular trap adapted to catch the resilient bolting snap of the socket. The assembly is obtained by inserting the plug into the socket whereby the cylindrical part of the plug lifts the resilient bolting snap which then falls down behind the cylindrical part to be caught by the cylindrical part to lock the assembly. As a result, this connection is not detachable. And for small diameters the socket and its resilient bolting snap is difficult to manufacture. It may be therefore difficult to achieve reliably reproducible snapping and locking forces on randomly combined guidewires and extensions.

It is an object of this invention to improve the possibilities of attaching an extension wire to a guidewire and to avoid the aforesaid drawbacks. Still a further object of the invention is to achieve attachment and release of a guidewire and extension wire by means of a docking assembly which is simple, inexpensive and easy to manufacture, which guarantees a smooth, efficient and repetitive operation for both connection and release of the guidewire and extension wire, and which does not require skills or troublesome manipulations, and which provides reliably reproducible locking and unlocking conditions on randomly combined guidewires and extensions.

SUMMARY OF THE INVENTION

As opposed to the aforesaid prior art systems, the docking assembly according to the present invention constitutes a true lock providing a positive locking action and direct unlocking which do not rely on hazardous friction arrangements and the like. Full repetition of the locking and unlocking operations is assured. And such a positive action is obtained without any additional tools such as pliers and the like.

Docking is simply achieved by insertion of the bolt means into the socket means and mere pushing of said bolt means against the bias of the spring means of the plug means up to catching of the bolt means by the trap means under the bias of the spring means generating a force urging the bolt means into the trap means. To unlock the assembly, it suffices to pull the bolt means out from the socket means, which is merely the operation opposite to the docking; the force needed for locking and unlocking is therefore the same. No skills are needed and no time consuming manipulations, either. Just simple movements which do not require any special training.

As the spring force of the system is a result of the bending strength of the plug means, the assembly can easily reach the small dimensions required for guidewires and extension wires. Furthermore, the spring force of the system may be determined in a wide spectrum without tolerance or size problems, and it remains practically out of the influence of environmental conditions.

In sum, the present invention relates to a docking assembly for the extension of a guidewire with an extension wire, comprising socket means and plug means for axial engagement into said socket means. The assembly may be characterized in that it comprises bolt means on said plug means, trap means in said socket means for catching said bolt means, and spring means on said plug means generating a spring force to urge the bolt means into the trap means. The spring means may be formed by a length of the plug means whereby the spring force is a result of the bending strength of the length of the plug means. The trap means may be formed by a shoulder protruding on the inside of the socket means. The docking assembly may further comprise ramp means in said socket means cooperating with said shoulder means for directing said bolt means into the socket means against the bias of said spring means and for thereafter positioning said bolt means towards said shoulder under the bias of said spring means. The shoulder may have a supporting face for said bolt means which is substantially way giving to said bolt means. Abutment means may be configured on said plug means for limiting engagement of said bolt means into said socket means.

The present invention also relates to a guidewire attachment assembly having: (a) an elongated member having a nonuniform outer surface defining at least one recessed area; (b) a tubular member having an inner surface forming a lumen adapted to receive the elongated member; and (c) at least one resilient member projecting from the inner surface of the tubular member into the lumen, the at least one resilient member adapted to deflect from a first position and then at least partially return toward the first position such that the resilient member is disposed at least in part within the at least one recessed area of the elongated member. The at least one resilient member may be adapted to deflect from a first position upon insertion of the elongated member into the tubular member, and further adapted to at least partially return toward the first position upon further insertion of the elongated member into the tubular member. The elongated member may have a tip ending in a shoulder, wherein upon insertion of the elongated member a predetermined distance into the tubular member the shoulder engages the resilient member. The shoulder may have a surface forming an imaginary angle with the inner surface of the tubular member, and the at least one resilient member may have a surface forming about the same imaginary angle with the inner surface of the tubular member when in its at least partially returned position. The angles α and α' are shown in FIGS. 7 and 8. These angles formed from shoulder 6' and/or face 6 may be the same or different from each other, and may be from about 95° to about 175°, or about 105° to about 165°, or about 135°.

The present invention also relates to a guidewire attachment assembly having: a) an elongated member having a distal end and a proximal end, the elongated member having a nonuniform outer surface defining at least one recessed area located a predetermined distance from the distal end; b) a tubular member having a distal end and a proximal end and an inner surface forming a lumen adapted to receive the elongated member; c) a first resilient member projecting from the inner surface of the tubular member into the lumen, the first resilient member adapted to deflect from a first position and then at least partially return toward the first position such that the first resilient member is disposed at least in part within the at least one recessed area of the elongated member; and d) a second resilient member projecting from the inner surface of the tubular member into the lumen. the second resilient member adapted to deflect from a second position to engage the distal end of the tubular member.

The present invention also relates to a method for releasably connecting an elongated member to a tubular member. The method consists of: (a) inserting an elongated member into a tubular member. wherein the elongated member has a nonuniform outer surface defining at least one recessed area. and wherein the tubular member has an inner surface forming a lumen adapted to receive the elongated member and having at least one resilient member projecting from the inner surface of the tubular member into the lumen and maintaining a first position; (b) pushing the elongated member into the tubular member so that the elongated member makes contact with the at least one resilient member thereby deforming the at least one resilient member so that it assumes a second position; and (c) continuing to push the elongated member so that the at least one resilient member at least partially returns toward the first position such that the at least one resilient member assumes a third position disposed at least in part within the recessed area of the elongated member.

The present invention also relates to a method for releasably connecting an elongated member to a tubular member. The method consists of: (a) inserting an elongated member into a tubular member, wherein the elongated member has a nonuniform outer surface defining at least one recessed area, and wherein the tubular member has an inner surface forming a lumen adapted to receive the elongated member and having a first resilient member projecting from the inner surface of the tubular member into the lumen and maintaining a first position and a second resilient member projecting from the inner surface of the tubular member into the lumen and maintaining a second position; (b) pushing the elongated member into the tubular member so that the elongated member makes contact with the first resilient member thereby deforming the first resilient member so that it assumes a second position; and (c) continuing to push the elongated member so that the second resilient member deforms and engages the distal end of the tubular member and the first resilient member at least partially returns toward the first position such that the resilient member assumes a third position disposed at least in part within the recessed area of the elongated member.

These and other features will become readily apparent from the following detailed description with reference to the accompanying drawings which show, diagrammatically and by way of example, a preferred embodiment of the invention and a variant thereof.

DESCRIPTION OF THE PREFERRED EMBODIMENTS

Figure 1:
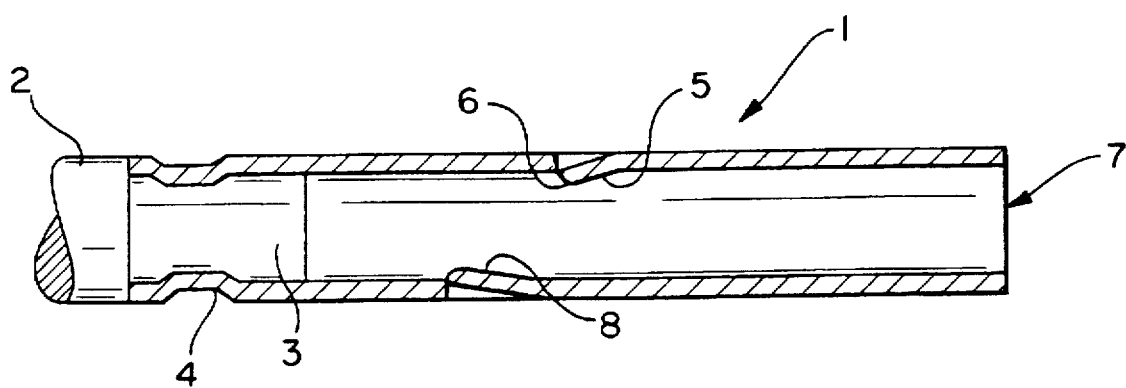
FIG. 1 is a longitudinal sectional view of a socket means of the present invention.

The socket means shown in FIG. 1 is formed of a tubing 1 which is preferably made of the same material as the guidewire 2 for biocompatibility reasons. The tubing 1 is engaged on the proximal end 3 of the guidewire 2 which has been appropriately ground to take up the thickness of the tubing 1. The tubing 1 is secured to the proximal end of the guidewire by a crimping 4. Other attachments are possible, such as for example by welding.

Inside the tubing 1 is a trap means formed by a substantially rigid shoulder 5 protruding on the inside of the socket means and which may be obtained by punching the wall of tubing 1. Preferably, this punching is made to define on shoulder 5 a supporting face 6 which is substantially oriented in a direction opposite to the free end 7 of tubing 1.

Also inside the tubing 1 is a ramp 8 which is some distance apart from shoulder 5, in the direction opposite to the free end 7 of tubing 1. Ramp 8 may also be made by punching the wall of tubing 1.

Figure 2:
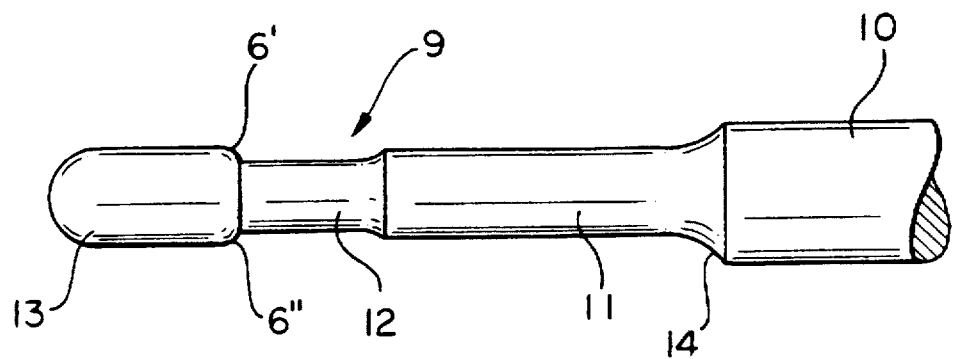
FIG. 2 is a longitudinal view of a plug means of the present invention.

The plug means 9 shown in FIG. 2 are formed by grinding the distal end of extension wire 10. Extension wire 10 may be made of stainless steel or other alloys typically employed in the art. Instead of grinding the distal end of extension wire 10, it is however possible to have plug means 9 fitted to the appropriately ground distal end of extension wire, for example by crimping or welding.

Plug means 9 include a resilient longitudinal shaft 11 having a narrower extension 12 terminating as a bolt means 13. Junction of shaft 11 with the extension wire 10 acts as a shoulder or abutment 14.

Figure 3:
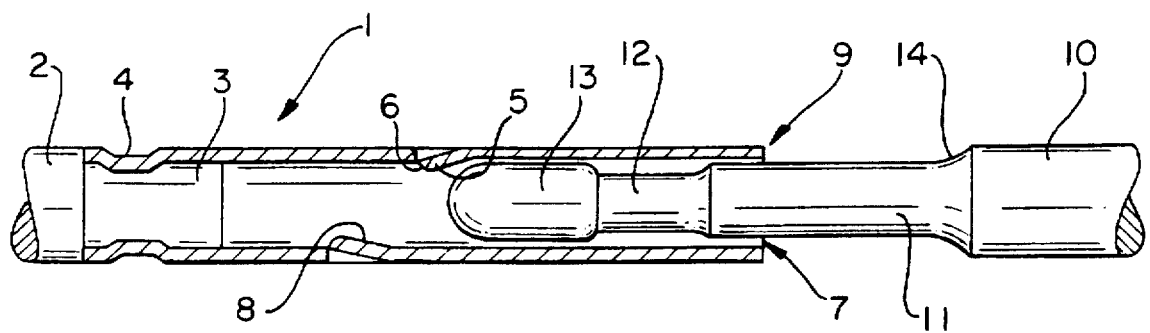
FIGS. 3, 4 and 5 are longitudinal sectional views showing assembly of the elements of FIGS. 1 and 2.
Figure 4:
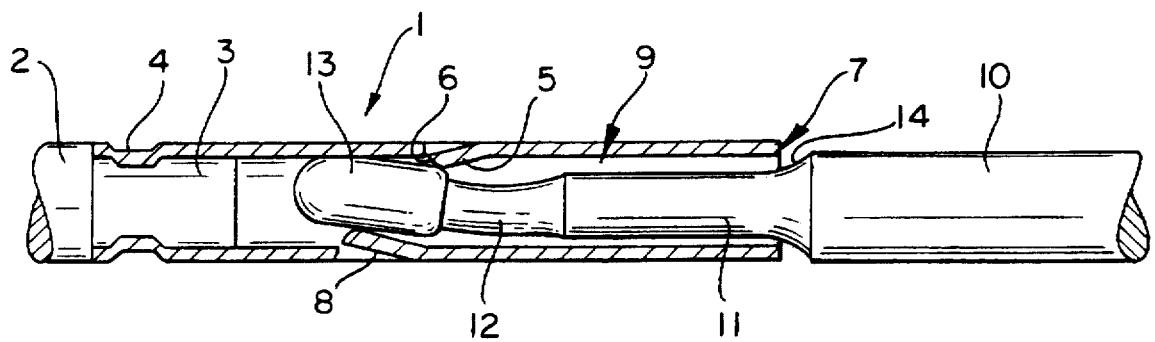
Figure 5:
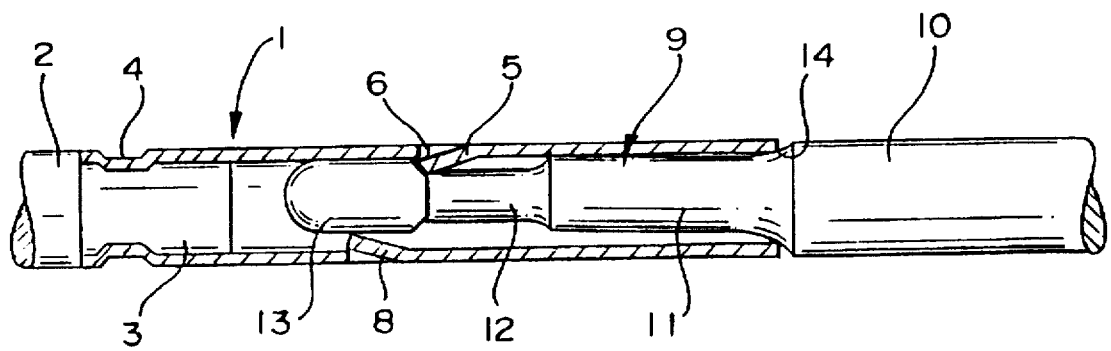

FIGS. 3, 4 and 5 illustrate the assembly of plug means 9 and tubing 1. The bolt 13 is initially inserted into the free end 7 of tubing 1 and the plug means 9 are merely pushed until the fore-end of bolt 13 encounters shoulder 5 and ramp 8.

As shown in FIG. 4, ramp 8 cooperates with shoulder 5 to incline upwardly bolt 13 and direct it through the constriction formed by ramp 8 and shoulder 5. This inclination of bolt 13 causes the narrow extension 12 to bend arcuately as shown in FIG. 4, and therefore the inclination of bolt 13 occurs against the resilient bias of shaft 11 and its narrow extension 12.

Once the rear end of bolt 13 has exceeded the edge of shoulder 5 the resiliency of shaft 11 and its narrow extension 12 sets up again the bolt 13 the rear end of which bears against supporting face 6 of shoulder 5, as shown in FIG. 5. At that stage, abutment 14 at the junction of shaft 11 with the extension wire 10 bears against the free end 7 of tubing 1 and prevents over engagement of the bolt 13 into the tubing 1, thereby avoiding needless play in the assembly.

Accordingly, the trap means 5 in the socket means 1 are catching the bolt means 13 and the spring means 11, 12 are generating a spring force which urges the bolt means into the trap means. Furthermore, as the spring means are formed by a length of the plug means 9, the spring force is a result of the bending strength of the length of the plug means 9.

Unlocking of the assembly is exactly the reverse operation and, due to its orientation, supporting face 6 of shoulder 5 gives way to the bolt 13, thereby avoiding any risk of hooking bolt 13 against shoulder 5.

Variants may be envisaged.

Instead of having the socket means affixed to the proximal end of the guidewire, and the plug means affixed to the distal end of the extension wire as shown in FIGS. 1 to 5, it is possible to have the socket means affixed to the distal end of the extension wire and the plug means affixed to the proximal end of the guidewire. It may be noted, however, that the arrangement shown in FIGS. 1 to 5 is preferred because it avoids having the tiny plug means at the proximal end of the guidewire and the resulting risk of damaging a balloon catheter at the engagement thereof over the guidewire. Furthermore, the presence of the socket means at the proximal end of the guidewire avoids further treatment thereof such as for instance polishing, and also gives a greater handiness for operating the proximal end of the guidewire.

A further variant provides for suppressing the shoulder 14 as a specific abutment limiting the engagement of bolt 13 into the tubing 1, the bolt 13 being then relatively free to advance into the tubing 1 until it encounters the proximal end 3 of the guidewire.

Figure 6:
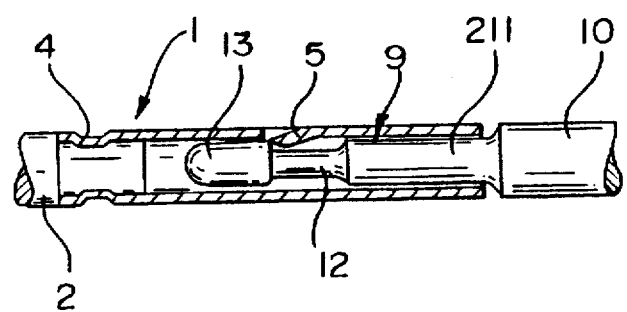
FIG. 6 is a longitudinal view showing an assembly variant.
Figure 7:
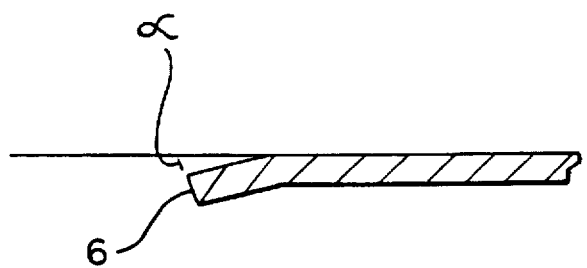
FIGS. 7 and 8 show angles α and α'.
Figure 8:
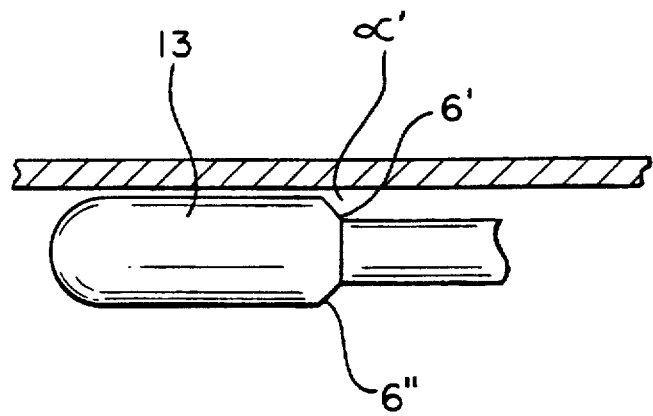

Another variant suppresses the ramp 8, whereby directing and positioning of the bolt into the tubing will be achieved by a grater diameter of the shaft 11 in order to get a drive from the tubing 1. FIG. 6 shows this configuration with the same elements bearing the same reference numerals as in FIGS. 1 to 4, and enlarged shaft 211. Here again, the trap means formed by the shoulder 5 protruding inside the socket means 1 are catching the bolt means 13, and the spring means 211, 12 are generating a spring force which urges the bolt means 13 into the trap means. And due to the spring means formed by a length of the plug means 9, the spring force is also a result of the bending strength of the length of the plug means 9.

According to a further variant, the shoulder 5 may have an edge 6 which is oriented otherwise than for giving way to the bolt 13, this function, if needed, being assured by the shape of the bottom of the bolt 13.

The foregoing specification and accompanying figures are provided to illustrate, and not limit, the present invention.

I claim:

1. A guidewire attachment assembly comprising:
   (a) an elongated member having a resilient longitudinal shaft having a nonuniform outer surface defining at least one recessed area;
   (b) a tubular member having an inner surface forming a lumen adapted to receive the elongated member; and
   (c) at least one substantially rigid member projecting from the inner surface of the tubular member into the lumen, said at least one rigid member adapted to deflect said resilient longitudinal shaft from a first position and then to at least partly allow return of the resilient longitudinal shaft towards the first position such that the at least one rigid member is disposed at least in part within the at least one recessed area of the resilient longitudinal shaft.

2. The guidewire attachment of claim 1, wherein the at least one rigid member is adapted to deflect the resilient longitudinal shaft from the first position upon insertion of the elongated member into the tubular member, and further adapted to at least partly allow return of the resilient longitudinal shaft towards the first position upon further insertion of the elongated member into the tubular member.

3. The guidewire attachment of claim 1, wherein the resilient longitudinal shaft has a tip ending in a shoulder, wherein upon insertion of the elongated member a predetermined distance into the tubular member the shoulder engages the at least one rigid member.

4. The guidewire attachment of claim 3, wherein the shoulder has a flat surface forming an imaginary angle with the inner surface of the tubular member when the resilient longitudinal shaft is in its first position, and the at least one rigid member has a flat surface forming about the same imaginary angle with the inner surface of the tubular member, the shoulder flat surface and the rigid member flat surface adapted to make contact with one another along the flat surfaces.

5. A guidewire attachment assembly comprising:
   (a) an elongated member having a resilient longitudinal shaft having a distal end portion and a proximal end portion, the resilient longitudinal shaft having a nonuniform outer surface defining at least one recessed area located a predetermined distance from the distal end portion;
   (b) a tubular member having a distal end and a proximal end and an inner surface forming a lumen adapted to receive the elongated member;
   (c) at least one substantially rigid member projecting from the inner surface of the tubular member into the lumen; and
   (d) ramping means projecting from the inner surface of the tubular member into the lumen, said ramping means adapted to cooperate with said at least one rigid member to deflect said resilient longitudinal shaft from a first position and then to allow return of the resilient longitudinal shaft towards the first position such that the at least one rigid member is disposed at least in part within the at least one recessed area of the resilient longitudinal shaft and the ramping means engages the distal end portion of the resilient longitudinal shaft.

6. The guidewire attachment of claim 5, wherein the at least one rigid member and the ramping means are adapted to deflect the resilient longitudinal shaft from the first position upon insertion of the elongated member into the tubular member, and further adapted to allow return of the resilient longitudinal shaft towards the first position upon further insertion of the elongated member into the tubular member.

7. The guidewire attachment of claim 5, wherein the ramping means is adapted to engage the distal end portion of the resilient longitudinal shaft such that the ramping means pushes the distal end portion of the resilient longitudinal shaft towards the inner surface of the lumen.

8. The guidewire attachment of claim 5, wherein the resilient longitudinal shaft has a tip ending in a shoulder, wherein upon insertion of the elongated member a predetermined distance into the tubular member the shoulder engages the at least one rigid member.

9. The guidewire attachment of claim 8, wherein the shoulder has a flat surface forming an imaginary non-perpendicular angle with the inner surface of the tubular member when the resilient longitudinal shaft is in its first position, and the at least one rigid member has a flat surface forming about the same imaginary non-perpendicular angle with the inner surface of the tubular member, the shoulder flat surface and the rigid member flat surface adapted to make contact with one another along the flat surfaces.

10. The guidewire attachment of claim 7, wherein the ramping means is located a distance apart from the at least one rigid member along the tubular member.

11. A method for releasably connecting an elongated member to a tubular member, the method comprising:
   (a) inserting an elongated member into a tubular member, wherein the elongated member has a resilient longitudinal shaft having a nonuniform outer surface defining at least one recessed area, and wherein the tubular member has an inner surface forming a lumen adapted to receive the elongated member and comprising at least one substantially rigid member projecting from the inner surface into the lumen;

(b) pushing the elongated member into the tubular member so that the resilient longitudinal shaft makes contact with the at least one rigid member and the at least one rigid member thereby deflects the resilient longitudinal shaft from a first position; and (c) continuing to push the elongated member into the tubular member so that the resilient longitudinal shaft at least partly returns towards the first position such that the at least one rigid member is disposed at least in part within the at least one recessed area of the resilient longitudinal shaft.

12. The method of claim 11, wherein the resilient longitudinal shaft has a tip ending in a shoulder, wherein upon insertion of the elongated member a predetermined distance into the tubular member the shoulder engages the at least one rigid member.

13. The method of claim 12, wherein the shoulder has a flat surface forming an imaginary non-perpendicular angle with the inner surface of the tubular member when the resilient longitudinal shaft is in its first position, and the at least one rigid member has a flat surface forming about the same imaginary angle with the inner surface of the tubular member, the shoulder flat surface and the rigid member flat surface adapted to make contact with one another along the flat surfaces.

14. A method for releasably connecting an elongated member to a tubular member, the method comprising:

(a) inserting an elongated member into a tubular member wherein the elongated member has a resilient longitudinal shaft having a distal end portion and a proximal end portion and a nonuniform outer surface defining at least one recessed area, and wherein the tubular member has an inner surface forming a lumen adapted to receive the elongated member and comprising at least one substantially rigid member projecting from the inner surface into the lumen and ramping means projecting from the inner surface of the tubular member into the lumen;

(b) pushing the elongated member into the tubular member so that the distal end portion of the resilient longitudinal shaft makes contact with the at least one rigid member and ramping means and the at least one rigid member and ramping means thereby deflect the resilient longitudinal shaft from a first position; and (c) continuing to push the elongated member into the tubular member so that the resilient longitudinal shaft returns towards the first position such that the at least one rigid member is disposed at least in part within the at least one recessed area of the resilient longitudinal shaft and the ramping means engages the distal end portion of the resilient longitudinal shaft.

15. The method of claim 14, wherein the resilient longitudinal shaft has a tip ending in a shoulder, wherein upon insertion of the elongated member a predetermined distance into the tubular member the shoulder engages the at least one rigid member.

16. The method of claim 15, wherein the shoulder has a flat surface forming an imaginary non-perpendicular angle with the inner surface of the tubular member when the resilient longitudinal shaft is in its first position, and the at least one rigid member has a flat surface forming about the same imaginary non-perpendicular angle with the inner surface of the tubular member, the shoulder flat surface and the rigid member flat surface adapted to make contact with one another along the flat surfaces.

17. The method of claim 14, wherein the ramping means is located a distance apart from the at least one rigid member along the tubular member.

18. The method of claim 14, wherein the ramping means is adapted to engage the distal end portion of the resilient longitudinal shaft such that the ramp pushes the distal end portion of the resilient longitudinal shaft towards the inner surface of the lumen.

19. A docking assembly for the extension of a guidewire with an extension wire, comprising socket means, plug means for axial engagement into said socket means, bolt means on said plug means, and trap means in said socket means for catching said bolt means, wherein said spring means on said plug means generates a spring force to urge the bolt means into the trap means.

20. The docking assembly of claim 19 wherein the spring means are formed by a length of the plug means whereby the spring force is a result of the bending strength of the length of the plug means.

21. The docking assembly of claim 19 wherein the trap means are formed by a shoulder protruding on the inside of the socket means.

22. The docking assembly of claim 21 further comprising ramp means in said socket means cooperating with said shoulder for directing said bolt means into the socket means against the bias of said spring means and for thereafter positioning said bolt means towards said shoulder under the bias of said spring means.

23. The docking assembly of claim 21 wherein said shoulder has a supporting face for said bolt means which is substantially way giving to said bolt means.

24. The docking assembly of claim 19 further comprising abutment means on said plug means for limiting engagement of said bolt means into said socket means.

25. The guidewire attachment assembly of claim 1 further comprising:

(d) a second substantially rigid member offset proximally of the at least one substantially rigid member and projecting from the inner surface of the tubular member into the lumen.

26. The guidewire attachment assembly of claim 5 further comprising:

(d) a second substantially rigid member offset proximally of the at least one substantially rigid member and projecting from the inner surface of the tubular member into the lumen.

* * * * *